United States Patent
Breton et al.

(10) Patent No.: US 11,809,488 B2
(45) Date of Patent: Nov. 7, 2023

(54) METHOD AND SYSTEM FOR GENERATING A PERSONALIZED PLAYLIST OF SOUNDS

(71) Applicant: MYBRAIN TECHNOLOGIES, Issy-les-Moulineaux (FR)

(72) Inventors: Audrey Breton, Paris (FR); Yohan Attal, Paris (FR)

(73) Assignee: MYBRAIN TECHNOLOGIES, Issy-les-Moulineaux (FR)

( * ) Notice: Subject to any disclaimer, the term of this patent is extended or adjusted under 35 U.S.C. 154(b) by 176 days.

(21) Appl. No.: 17/623,921

(22) PCT Filed: Jul. 7, 2020

(86) PCT No.: PCT/EP2020/069106
§ 371 (c)(1),
(2) Date: Dec. 30, 2021

(87) PCT Pub. No.: WO2021/005048
PCT Pub. Date: Jan. 14, 2021

(65) Prior Publication Data
US 2022/0365964 A1    Nov. 17, 2022

Related U.S. Application Data

(60) Provisional application No. 62/871,296, filed on Jul. 8, 2019.

(51) Int. Cl.
*G06F 16/635* (2019.01)
*G06F 16/638* (2019.01)
(Continued)

(52) U.S. Cl.
CPC ............ *G06F 16/635* (2019.01); *A61B 5/165* (2013.01); *A61B 5/291* (2021.01); *A61B 5/372* (2021.01);
(Continued)

(58) Field of Classification Search
CPC ....... A61B 5/7246; A61B 5/165; A61B 5/291; A61B 5/372; A61B 5/38; G06F 16/639; G06F 16/635
See application file for complete search history.

(56) References Cited

U.S. PATENT DOCUMENTS

2017/0140049 A1 * 5/2017 Chefalas ................. G06F 3/015
2017/0339484 A1   11/2017 Kim
2019/0247662 A1 * 8/2019 Poltroak ............ A61N 1/36053

OTHER PUBLICATIONS

Clerico et al., "Electroencephalography amplitude modulation analysis for automated affective tagging of music video clips"; Frontiers in computational neuroscience; 2018; vol. 11, Article 115; pp. 1-13.
(Continued)

*Primary Examiner* — Etienne P Leroux
(74) *Attorney, Agent, or Firm* — Maier & Maier, PLLC

(57) ABSTRACT

A method for generating for a subject a personalized playlist of sounds, notably songs, using the analysis of the subject's electroencephalographic signal, the method including the following steps: receiving at least one segment of electroencephalographic signal acquired from at least one electrode while the subject is listening to at least one proposed sound; extracting at least one EEG index from the electroencephalographic signal segment so as to characterize brain patterns correlated to the emotions evoked by the music and the level of appreciation of the sound; evaluating the valence of sounds listening on the basis of the EEG index; receiving a score of appreciation on the sound from the subject; including the sound in the personalized playlist (P) of the subject whenever the valence matches a predefined valence and/or the score of appreciation is higher than a predefined threshold.

15 Claims, 8 Drawing Sheets

(51) Int. Cl.
  *A61B 5/372* (2021.01)
  *A61B 5/291* (2021.01)
  *A61B 5/16* (2006.01)
  *A61B 5/00* (2006.01)
  *A61B 5/38* (2021.01)
(52) U.S. Cl.
  CPC .............. *A61B 5/38* (2021.01); *A61B 5/7246* (2013.01); *G06F 16/639* (2019.01)

(56) References Cited

OTHER PUBLICATIONS

Koelstra et al., "Single trial classification of EEG and peripheral physiological signals for recognition of emotions induced by music videos"; International Conference on Brain Informatics; 2010; pp. 89-100.

International Search Report dated Sep. 11, 2020 in corresponding International Patent Application No. PCT/EP2020/069106; 5 pages.

* cited by examiner

METHOD AND SYSTEM FOR GENERATING A PERSONALIZED PLAYLIST OF SOUNDS

FIELD OF INVENTION

The present invention relates to the field of neuroscience. In particular, the present invention relates to the field of analysis of the electrophysiological signal of a subject to characterize brain patterns so as to follow the emotions evoked by the music and his dependence on the individual appraisal of a song.

BACKGROUND OF INVENTION

Nowadays, with the advent of the music streaming services, having a personal playlist is a common custom; users select songs from a multitude of possibilities, storing them in a list of favorites. The strategies that determine the choice of some songs rather than others is a topic considered interesting in many different sectors of the musical industry. In this respect, the aim of the present research is to study whether the individual emotional state could be one of the influence factors in the process of musical evaluation. Two experiment were conducted in this research. In the first experiment we employed electrophysiological signals to characterize brain patterns able to follow the emotions evoked by the music and their dependence on the individual appraisal of the songs. In a second experiment, through psychometric measures, we studied whether the emotional state of participants could affect the choice of songs they decided to listen to. Previous researches already explored the pleasantness experienced in listening to songs, however they considered it as consequence of the emotions evoked by the music. They generally assumed that brain patterns sensible to follow the valence, positive or negative, of the emotions, could reveal the level with which the songs were enjoyed from the listeners. However, it is reasonable to assume that listeners could enjoy a song irrespective of the emotions it evokes. For instance, brain responses associated to negative emotions are not necessarily significant for a disliking condition: people could enjoy the listening of negative songs, even considering them as favorite. Therefore, in the present study, the emotional valence and the musical appraisal were considered as separated factors.

The advent of the music streaming services made possible the free access, in every moment, to every kinds of song. By creation of playlists, users store the songs they mostly like in personal music libraries, readily available. Exploring the brain signature of musical listening, to define a reliable method for determining and predicting the songs' appreciation and their potential inclusion in personal playlists. Through the analysis of electroencephalographic (EEG) signals, the present study aimed at characterizing the emotional response to music, one of the factors that might be crucial in the process of songs selection. Additionally, the link between emotions and the level with which music is liked was explored.

The relation between music and emotions has been the focus of a huge amount of researches in many different disciplines. Listening to music showed to be strongly related to the experience of emotions, at the point that some musicologists have even hypothesized that the meaning of music consists properly in its ability of moving listeners.

In the field of neuroscience a broad literature already demonstrated that brain regions generally involved in processing emotions are activated while listening to music using the positron emission tomography (PET), showed that music employed to induce pleasant emotions and chills activated some emotion-related brain areas, such as amygdala and hippocampus. In the same way, through an fMRI study, it was found that limbic and paralimbic structures involved on emotional response, comprising the amygdala, hippocampus, parahippocampal gyrus and temporal poles, responded to both pleasant and unpleasant musical stimulation. Despite neuroimaging techniques provide information about specific brain areas involved in specific cognitive processes, the EEG analysis results more efficient to study regional and global interactions among brain areas. Furthermore, in the context of musical experience, EEG is preferable to follow the temporal changes induced during prolonged periods of musical stimulation. One of the approaches for the emotion recognition through EEG, is correlating brain activation patterns to variations of two emotional dimensions: valence and arousal. The arousal-valence dimensional model was conceived by Russel (Russell, 1980), it is a continuous two-dimensional circular space, in which emotions can be represented as a vector, whit arousal and valence as axes. Valence describes whether the emotions are negative or positive; while the arousal indicates the intensity, high or low, with which the emotions are felt. The musical features, such as mode and tempo, could have impact on the type of emotions music might convey. In particular, the musical mode modulation has been linked to the valence of the emotions felt: major mode fosters positive feelings while minor mode tends to induce negative feelings. Musical tempo, instead, was linked to the arousal: increased frontal activation, was found for faster tempo, especially in the left hemisphere and it was associated to the increasing of emotional intensity. In the EEG analysis, one of the methods to evaluate the emotional valence is the approach-withdrawal index (AW). The Davidson's approach-withdrawal theory assumes the valence of the felt emotions can be sought in specific cortical activation patterns, in the range of frequency to which alpha waves oscillate (from 8 to 12 Hz). In particular, he demonstrated that higher electrical activity in left frontal region, compared to the right one, might be associated to the experience of positive emotions (approach tendency). An opposite frontal asymmetry is conversely related to negative emotions (withdrawal tendency). This index showed its sensitivity in several contexts and interestingly it demonstrated to well characterize the emotional response to music. Generally, the protocol employed in these experiments includes at first a phase of song selection in which musical excerpts are chosen for their average tendency of evoking positive or negative emotions. Secondly in the experimental phase, the excerpts are employed as stimuli for all the participants while their brain activity is recorded. With the view of computing the AW index (Allen, Coan, & Nazarian, 2004), it is worth to note that Schmidt and Hanslmayr (B. Schmidt & Hanslmayr, 2009) showed that frontal alpha asymmetry in resting state might affect the stimuli evaluation in terms of valence and liking. Specifically, they found that left active participants, which had a frontal alpha asymmetry at resting state tending to the left, rated all musical stimuli as more positive than the right active participants.

Although many evidences addressed the emotional response to alpha power modulation, not all the studies succeeded in finding significant results using this approach. Another EEG parameter that showed its sensibility to the emotional valence is the frontal midline theta power activity. Specifically, increased frontal midline theta power was found for the exposure to music associated to positive emotions. Modulations of the frontal midline theta power have been linked to the cerebral metabolism in the anterior cingulate cortex ACC, which is part of the limbic system engaged in emotional and attentional mechanisms. The arousal detection at the EEG level is still uncertain. Previous findings showed that the intensity of the emotions felt can be sought in the power over all frontal regions, which is assumed to increase with the increasing of the emotional intensity.

Once the strategy for evaluating the emotional response was clearly identified, an additional aspect was considered in this study: the musical liking. The investigation of this factor was encouraged by the idea that users could enjoy the listening of songs independently from the feelings they evoke. For instance, despite their negative emotional valence, sad excerpts are commonly included among songs users mostly like.

Due to the considerations of the stat of the art, the brain response to music in the present invention was investigated not only in terms of emotions, positive or negative but also in terms of liking. Two degrees of liking have been considered in the study, differentiating songs that participants simply liked and favorite songs labeled as loved. In order to capture a significant and spontaneous reaction to music, we established to employ subjective musical stimuli. Following our instructions, participants were asked to choose from their playlists some songs responding to specific characteristics of valence and liking. This experimental strategy was previously followed by other researchers, such as Adamos and his colleagues (Dimitrios A. Adamos, Stavros I. Dimitriadis, & Nikolaos A. Laskaris, 2016) which employed subjective musical stimuli to investigate, through EEG analysis, the aesthetic appreciation of a piece of music. The impact of the musical liking at the brain level was not clearly defined, due to the lack of past researches on this topic.

SUMMARY

The present invention relates to a method for generating for a subject a personalized playlist of sounds, notably songs, using the analysis of the subject's electroencephalographic signal (EEG), said method comprising the following steps:
  receiving at least one segment of electroencephalographic signal acquired from at least one electrode while the subject is listening to at least one proposed sound;
  extracting at least one EEG index from the electroencephalographic signal segment so as to characterize brain patterns correlated to the emotions evoked by the music and the level of appreciation of the sound;
  evaluating the valence of sound listening on the basis of the EEG index;
  receiving a score of appreciation on the sound from the subject;
  including the sound in the personalized playlist of the subject whenever the valence matches a predefined valence and/or the score of appreciation is higher than a predefined threshold.

Advantageously, the valence evaluation reflects the emotional reaction of the subject to the sound.

According to one embodiment, the method of the present invention is a computer implemented method.

According to one embodiment, the at least one EEG index is chosen among the following: Approach-Withdrawal index, the Frontal-Midline theta index, the prefrontal alpha power and/or the right parietal alpha power.

According to one embodiment, the method comprises a step of discarding the sound whenever the deviation between the valence and the predefined valence is higher than a predefined threshold and/or the score of appreciation is lower than a predefined threshold.

According to one embodiment, the proposed sound is selected from a database of sound and it is unknown to the subject.

According to one embodiment, the proposed sound is selected from the database of sound using a sound selection algorithm, said sound selection algorithm being configured to identify in the sounds comprised in the personalized playlist, on the basis of the score of appreciation, at least one specific pattern and select from the database of sound at least one sound with a similar specific pattern.

The method of the present invention allows advantageously to generate a personalized playlist that suites the musical taste of a subject thanks to the extraction of objective EGG indexes from the EEG signal registered during the listening of the music. Indeed, the evaluation of sounds appreciation via EEG (i.e. valence of sound listening on the basis of the EEG index) is more accurate and less biased than when is obtained from an evaluation of the subject itself.

According to one embodiment, each sound included in the playlist is stored in a personal database with the score of appreciation and the EEG index(es).

According to one embodiment, the method further comprises a machine learning algorithm configured to search, across databases of multiple subjects, for the presence of similar scores of appreciations and the EEG indexes for one sound. Whenever multiple matches in scores of appreciations and the EEG indexes for multiple sounds are detected between at least two subjects, the playlist of the one subject may be proposed to the other subject. In one example this embodiment may be used to generate a preliminary playlist of sound for a subject starting to use the method of the present invention and his/her personalized playlist is still not completed.

When the method has access to a large number of subject databases, the predefined threshold may be updated as function of the subject based on the subject profile information such as age, gender and the like.

The present invention further relates to a data processing system comprising means for carrying out the steps of the method according to any one of the embodiments described hereabove.

According to one embodiment, the system further comprises an acquisition module for acquiring at least a segment of electroencephalographic signals from a subject and an audio-headset for producing the sound.

Yet another aspect of the present invention concerns a computer program product for generating a personalized playlist of sounds using electroencephalographic signal analysis, the computer program product comprising instructions which, when the program is executed by a computer, cause the computer to carry out the steps of the method according to any one of the embodiments described hereabove.

The present invention further relates to a computer-readable storage medium comprising instructions which, when the program is executed by a computer, cause the computer to carry out the steps of the method according to any one of the embodiments described hereabove.

The present invention further relates to a method for selecting from a personalized playlist of sounds of a subject a sub-group of sounds according to the emotional state of the subject:

receiving an information concerning the subject's emotional state defined by the subject;

selecting at least one sound from the personalized playlist and play it to the subject;

receiving at least one segment of electroencephalographic signal acquired from at least one electrode while the subject is listening to the selected sound;

calculating the value of the Approach-Withdrawal index for the at least one segment of electroencephalographic signal;

whenever the Approach-Withdrawal index is greater that a predefined threshold, adding the selected sound to a sub-group of sounds associated to the type of emotional state defined by the subject.

Advantageously, calculating the value of the Approach-Withdrawal index allows to evaluate the response of the subject to the selected sound.

The present invention further relates to a data processing system comprising means for carrying out the steps of the method for selecting from a personalized playlist of sounds of a subject a sub-group of sounds according to the emotional state of the subject.

According to one embodiment, the system further comprises an acquisition module for acquiring at least a segment of electroencephalographic signals from a subject and an audio-headset for producing the sound.

The present invention further relates to a computer program product for selecting from a personalized playlist of sounds of a subject a sub-group of sounds, the computer program product comprising instructions which, when the program is executed by a computer, cause the computer to carry out the steps of the method for selecting from a personalized playlist of sounds of a subject a sub-group of sounds according to the emotional state of the subject.

The present invention further relates to a computer-readable storage medium comprising instructions which, when the program is executed by a computer, cause the computer to carry out the steps of the method for selecting from a personalized playlist of sounds of a subject a sub-group of sounds according to the emotional state of the subject.

Definitions

In the present invention, the following terms have the following meanings:

"Electroencephalogram" refers to the record of the electrical activity of the brain of a subject.

"Priming" refers to a technique whereby exposure to one stimulus influences a response to a subsequent stimulus, without conscious guidance or intention.

"Segment of EEG signal" refers to a portion of the EEG signal in a predefine time interval, comprising the signal of one or more electrodes.

"Valence" refers to is the affective quality referring to the intrinsic attractiveness/"good"-ness (positive valence) or averseness/"bad"-ness (negative valence) of an event, stimulus, object, or situation.

DETAILED DESCRIPTION

Features and advantages of the invention will become apparent from the following description of embodiments of a method and a system, this description being given merely by way of example.

Figure 8:
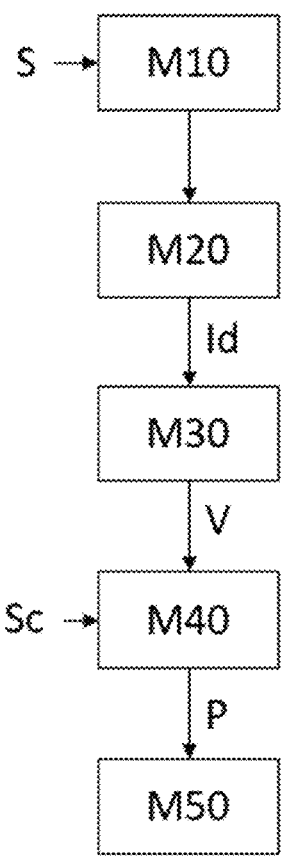
FIG. 8 is a block diagram representing the main steps of the method of the present invention.

The method and system of the present invention are based on the observation of the oscillatory components in alpha and theta band for the distinct conditions of liking, exploring as well the link with the emotional valence. FIG. 8 provides a schematic representation of the main steps of the method of the present invention.

According to one embodiment, the method comprises a step M10 of receiving at least one segment of electroencephalographic signal S acquired from at least one electrode while the subject is listening to at least one proposed sound.

According to one embodiment, the proposed sound is selected from a database of sounds and it is unknown to the subject. The sounds may be songs, or at least portions of songs. According to one embodiment, the proposed sound is selected from the database of sound using a sound selection algorithm, said sound selection algorithm being configured to identify in the sounds comprised in the personalized playlist, on the basis of the score of appreciation, at least one specific pattern and select from the database of sound at least one sound with a similar specific pattern.

According to one embodiment, the electroencephalographic signal received is recorded from at least two of electrodes, positioned onto predetermined areas of the scalp of the subject in order to obtain a multi-channel electroencephalographic signal.

According to one embodiment, the electroencephalographic signal is received in real time. According to another embodiment, the electroencephalographic signal is recorded during a predefined period of time and stored in a storage medium.

According to one embodiment, the electroencephalographic signal from individual scalp electrodes is digitally filtered with a bandpass filter selecting a specific range of frequencies or a notch filter.

According to one embodiment, the method further comprises a step M20 of extracting at least one EEG index Id from the electroencephalographic signal segment S so as to characterize brain patterns correlated to the emotions evoked by the music and the level of appreciation of the sound.

According to one embodiment, the EEG index Id is chosen among the following: Approach-Withdrawal index, the Frontal-Midline theta index, the prefrontal alpha power and/or the right parietal alpha power.

In one embodiment, the Approach Withdrawal index and the Frontal Midline Theta Power index are computed from the EEG signal recorded from the frontal regions.

According to one embodiment, the method further comprises a step M30 of evaluating the valence of sounds listening V on the basis of the EEG index Id.

According to one embodiment, the method further comprises a step M40 of receiving a score of appreciation Sc on the sound from the subject. The subject may provide this score of appreciation through a user interface wherein the score of appreciation is represent as a value into a predefined numerical range. The score of appreciation Sc may be as well chosen by the subject among a multiple choice of words associated to different level of appreciation. The score of appreciation Sc may be inputted as well at any other moment of the method but before the step M50.

According to one embodiment, the method further comprises a step M50 of including the sound in the personalized playlist P of the subject whenever the valence matches a predefined valence and/or the score of appreciation Sc is higher than a predefined threshold.

According to one embodiment, each sound included in the personalized playlist P is stored in a personal database with the score of appreciation Sc and the EEG index Id.

Musical stimuli tailored to the participants were employed: each participant had a personal dataset determined in a preliminary phase of musical selection. In it was ensured to capture a strong and spontaneous reaction to musical listening. Participants selected eight songs they knew very well: four songs they loved and four songs they simply liked. For each level of liking, two songs evoked emotions with positive valence and two with negative valence. In a second phase, EEG signals were recorded from seventeen participants while they were listening to their own musical excerpts. The analysis of these data was mainly focused on oscillatory components in theta band (3-8 Hz), alpha band (8-12 Hz) and beta band (12-30 Hz). Two neuro-indexes, known to be sensible to the emotion detection, were computed over frontal regions: the Approach Withdrawal (AW) and the Frontal Midline Theta Power (Fmt). Four main findings were significant for this study: i) both the AW and the Fmt indexes were modulated by the emotional valence of the songs; ii) the general alpha power assumed higher values for liked songs if compared to the loved ones, in both valence conditions; iii) the alpha asymmetry over parietal electrodes, for negative emotions, was differently modulated by the level of liking; vi) the general theta power over the right hemisphere assumed higher values for positive emotions, in both liking conditions, while, in the left hemisphere it assumed opposite patterns in dependence of the levels of liking: higher theta values corresponded to positive emotions for like condition and to negative emotions for love condition. These findings exhibited a good reliability of the indexes in detecting the emotional valence. Furthermore, although the effect of the liking condition was not found, many interactions between the emotional valence and the levels of liking, in both theta and alpha bands, were shown. The increasing of the general alpha power gave an indication about the intensity of the emotions felt. The songs considered as loved might have been able to induce stronger emotions than liked songs, whatever their valence was. The interactions found between emotional valence and liking conditions might have highlighted a difference of strategies, for loved and liked songs, in judging the emotional valence. It was assumed that participants could not avoid to rely on memories and personal experiences in evaluating songs they loved; although they were explicitly asked to base their judgments on musical features and lyrics. Therefore, the difference reaction we observed to musical stimulation might be sought in the hypothesis that some songs are loved right due to their association to the events of our life. The second experiment was designed to explore the way in which instantaneous personal feelings influence the choice of songs to listen to, in a precise moment. This aspect was investigated also in the first experiment, without showing significant result, probably because the emotional state of participants in the experimental context was excessively neutral. In order to capture stronger subjective feelings, participants were driven in a specific emotional state, through a phase of priming. This phase consisted in helping participants to recall past emotional experiences, moving them, alternatively in positive and negative emotional states. After the priming, people were asked to select a song they would like to listen to among their personal playlist (the playlists created in the first experiment). The results showed that participants tended to select songs having the same emotional valence of the priming they experienced. These findings were expected for the feelings of positive emotions but they were not for the negative ones. According to one hypothesis, after the priming for negative emotions, people might have needed to find relief in listening to songs that evoked positive emotions. On the contrary they chose to immerge themselves in the emotions they perceived, even whether they were negative. This phenomenon could be associated to the wish of release intimate feelings, expressing them out by the help of music. In this research it was pointed out that the level with which participants appreciate the songs might be related to the intensity of the emotions felt during the musical listening rather than their valence. Furthermore, we argued that the memories of past feelings associated or evoked by the musical listening could determine whether some songs are loved more than others. In conclusion it was showed that using the EEG it is possible to follow the emotional state of the user which is one of the main factors they rely on in musical evaluation. These findings pave the way to future automatic systems through which we could determine whether a song would access or not in playlists of targeting populations.

The present invention further relates to a computer program for generating a personalized playlist of sounds, the computer program product comprising instructions which, when the program is executed by a computer, cause the computer to carry out the steps of the computer-implemented method for generating a personalized playlist of sounds according to any one of the embodiments described hereabove in relation.

The present invention further relates to a computer program for selecting from a personalized playlist of sounds of a subject a sub-group of sounds according to the emotional state of the subject, the computer program product comprising instructions which, when the program is executed by a computer, cause the computer to carry out the steps of the computer-implemented method for selecting from a personalized playlist of sounds of a subject a sub-group of sounds according to the emotional state of the subject according to any one of the embodiments described hereabove in relation.

The invention also relates to a system for the processing of electroencephalographic signals comprising a data processing system comprising means for carrying out the steps of the method according to any one of the embodiments described hereabove.

According to one embodiment, the system further comprises an acquisition module for acquiring at least a segment of electroencephalographic signals from a subject. According to one embodiment, the acquisition set-up comprises any means known by one skilled in the art enabling acquisition (i.e. capture, record and/or transmission) of electroencephalographic signals as defined in the present invention, preferably electrodes or headset as explained hereabove. According to one embodiment, the acquisition module comprises an amplifier unit for magnifying and/or converting the electroencephalographic signals from analog to digital format.

According to one embodiment, the system comprises an output apparatus configured to output auditory stimuli such as audio headphones.

According to one embodiment, the data processing system is a dedicated circuitry or a general purpose computer device, configured for receiving the data and executing the operations described in the embodiment described above. Said computer device may comprise a processor and a computer program. The data processing system may include, for example, one or more servers, motherboards, processing nodes, personal computers (portable or not), personal digital assistants, smartphones, smartwatches, smartbands, cell or mobile phones, other mobile devices having at least a processor and a memory, and/or other device(s) providing one or more processors controlled at least in part by instructions.

The processor receives digitalized neural signals and processes the digitalized electroencephalographic signals under the instructions of the computer program to select the sounds in the playlist. According to one embodiment, the computing device comprises a network connection enabling remote implementation of the method according to the present invention. According to one embodiment, electroencephalographic signals wirelessly communicated to the data processing system. According to one embodiment, the output generator wirelessly receives the classes associated to the electroencephalographic signal segments from the data processing device.

The present invention further relates to a non-transitory computer-readable storage medium comprising instructions which, when the computer program is executed by a data processing system, cause the data processing system to carry out the steps of the method according to anyone of the embodiments described hereabove.

Computer programs implementing the method of the present embodiments can commonly be distributed to users on a distribution computer-readable storage medium such as, but not limited to, an SD card, an external storage device, a microchip, a flash memory device, a portable hard drive and software websites. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

While various embodiments have been described and illustrated, the detailed description is not to be construed as being limited hereto. Various modifications can be made to the embodiments by those skilled in the art without departing from the true spirit and scope of the disclosure as defined by the claims.

EXAMPLES

The present invention is further illustrated by the following examples.

Example 1

The pleasantness usually experienced by a subject while listening music was largely associated with, and also investigated through, the emotion the song conveys. However, one can love a very sad song and appraisal and valence has to be examined as separated factors.

Materials and Methods

The electrophysiological correlation of distinct degrees of music liking and their interaction with emotional valence was investigated using a bluetooth 8 dry-channel EEG headset. Seventeen participants were asked to classify familiar musical excerpts of their choice in two levels of preference ("liked" or "loved") considering negative or positive valence. Then, EEG signals were recorded while the participants listened to the excerpts.

The level of appraisal modulated alpha (8-13 Hz) power asymmetry in the parietal region, but only for negative excerpts. Emotion and liking interacted on theta oscillations (4-8 Hz):

Results

For positive emotion the highest theta power was found for liked songs, and for negative emotion, for loved ones.

Example 2

Materials and Methods

Participants

Seventeen healthy participants (five left-handed, eleven males), aged between 23 and 41 years old (mean age=28.82±5.14 SD, median=27), were recruited in this experiment. All of them reported normal hearing and they had no medical history of neurological disease. Participants were all employees of myBrain Technologies, with different musical education: five of them played an instrument from more than ten years. Before taking part at the experiment every participant gave his informed consent.

Stimuli

Stimuli set consisted in eight songs selected by the participants themselves. Each of them listened only to the songs he or she selected. In a preliminary phase, conducted twenty-five days before the EEG experiment, participants were asked to select eight excerpts from their personal playlist considering two main factors: i) the level with which they liked the songs and ii) the emotional valence they associated to those songs. In this experiment musical liking was defined by two general levels of songs' enjoyment: loving and simply liking. Furthermore, the emotional valence, has been assessed through two opposite definitions: positive or negative. Participants were asked to evaluate the musical valence relying only on the emotions evoked by musical features and lyrics. They were explicitly told that the feelings they perceived should not be related to any personal memories. At the end of the songs' selection, each participant had a subjective musical database, determined by four excerpts they loved, two for each emotional valence conditions and four they liked, two for each valence as well. Whether a part of a song was most representative for the target condition than the others, participants were asked to specify its corresponding timing. All the selected songs were imported in Reaper©, a software for digital audio manipulation (https://www.reaper.fm/), cut in 1-minute segment, applying six seconds of fade-in at the beginning and six seconds of fade-off at the end. All the excerpts were finally exported in WAV format.

Design and Procedures

The protocol employed in the present experiment can be schematized in three main phases: i) the self-assessment, ii) the EEG acquisition and iii) the songs' selection. For the whole experiment, participants were comfortably seated in front of a laptop, in a sound-proof room, wearing earbuds headphones. In the first phase, the self-assessment, participants filled out a PANAS questionnaire trying to evaluate their subjective positive and negative affects. The questionnaire was constituted by twenty items, depicting both positive and negative feelings. For each item, participants had to rate to what extent they felt in that way, using a 1 (very silently or not at all) to 5 (extremely) Likert scale. Afterward, the EEG acquisition phase had place. At first, signals were acquired for one-minute of resting state condition and one-minute of white noise listening. During the resting state, participants were asked to close their eyes, being quiet and relaxed, then, a one-minute white noise track was presented. Since this noise track was assumed to be neutral in terms of liking and emotional valence, it was used as a control stimulus. Secondly, the eight personal excerpts were played in a random order, while participants were keeping the eyes closed. The listening of each song was followed by a fifteen-seconds white noise sequence, trying to minimize the influence of two consecutive musical stimulations. The last phase of the experiment was designed to reproduce the process of musical selection among a playlist. The excerpts were divided in two groups: the group of loved songs (GROUP 1) and the group of liked songs (GROUP 2). Participants were asked to select a song they would like to listen to from each group, trying to figure them out of the experimental context, in a familiar place. They quickly listened to the excerpts of both groups being not aware of the criteria trough which songs were grouped. EEG was not recorded during this phase.

Electrophysiological Recordings

Electrophysiological data were recorded using an 8-channel Bluetooth headset developed internally by myBrain Technologies and connected to a tablet. The EEG headset was composed of eight dry electrodes, placed over the scalp at Fp1, Fp2, F3, F4, Fz, C3, P3 and P4 positions, according to the International 10-20 system. The ground was located on Cz and a supplementary electrode placed on the left earlobe was used as the reference. Signals were acquired at the sampling rate of 250 Hz (with an amplifying gain of 24, A/D converter resolution: 24 bits, input bias current: 1 pA) with no on-line filtering. All the EEG data were recorded and stored employing an application. This application enabled experimenters to visually check the trend of the signals over the entire duration of the acquisitions. In order to minimize the physiological artifacts on the signals, participants were warned about the importance of avoiding any body movement during the recordings.

EEG Data Processing

EEG data were analyzed in a MATLAB environment, employing the EEGlab toolbox for the signal processing. Signals were centered by removing their mean amplitude and they were filtered by a notch filter applied in 50 Hz and 100 Hz to remove the power line noise. Furthermore, a FIR band-pass filter between 2 and 40 Hz was applied in order to keep only the frequency band of interest. The muscular and eye movements were manually rejected by visual inspection. In average, 5.6% of the total signal was removed for each subject in this process.

Power spectral density was computed by the Welch method with 50% of overlap (Peter d. Welch, 1967). The processing was focused on theta (4-8 Hz) and alpha (8-12 Hz) bands. These frequency bands have been determined for each subject according to his individual alpha frequency (IAF) (Klimesch, 1999). The IAF was defined as the frequency corresponding to the maximum power value in the frequency band at which alpha activity generally oscillates (8-12 Hz) and it was determined at the posterior electrode P4, on the spectrum of the data acquired during the baseline. Theta band was defined from IAF−6 to IAF−4 while the alpha bandwidth was computed as IAF±0.2*IAF (Quaedflieg et al., 2016). Power in each frequency band was normalized according to the average power computed in the baseline (powerBS) using a decibel (dB) transform $$\left(dB_{Power} = 10 \log_{10} \frac{Power}{Power\ RS1}\right)$$

(Cohen and van Gaal 2013). Prior to the normalization, two neuro-indexes were estimated on alpha and theta band: the Approach Withdrawal index (AW) and the Frontal Midline Theta Power index (Fmt). The AW was computed as the difference of alpha power over the two prefrontal electrodes: AW=ln(Pow$_{\alpha Fp2}$)−ln(Pow$_{\alpha Fp1}$). This index was z-transformed (Quaedflieg et al., 2016) using mean values of the alpha asymmetry over the same electrodes in the baseline condition $$AW = \frac{AIstim - \text{mean}\ (AIbas)}{\sigma_{AIbas}},$$

where AI=ln(Pow$_{\alpha Fp1}$)−ln(Pow$_{\alpha Fp2}$) The Fmt was computed over the Fz electrode as the ratio of the mean theta power for each stimulus condition and the baseline condition:

$$FmtI = \frac{\text{mean}\ (PowStim_{\vartheta Fz})}{\text{mean}\ (PowBas_{\vartheta Fz})}$$

(S ammler, Grigutsch, Fritz, & Koelsch, 2007). The asymmetry of the alpha power was estimated also over frontal and parietal regions, employing the same computation operated for the AW. In addition, the difference between AW values for positive and negative emotions (ΔAW) was included in the correlation analysis. This ΔAW was defined as indicator of the brain sensitivity to the emotions felt.

Statistical Analysis

Statistical analyses were conducted using STATISTICA© software. Repeated measures of analysis of variance (ANOVA) were performed in order to determine the differences among mean values of EEG theta and alpha powers. At first, the label of the musical stimuli was designated as within-subject factors. In this context we considered two levels of emotional valence: positive and negative, and two levels of liking: loved and liked. However, when the analysis was led on different scalp regions, topographical factors, such as caudality (3 levels: prefrontal, frontal and parietal) and laterality (2 levels: left and right), were included among the within-subject factors. Fisher's low significant difference (LSD) test was employed for the post-hoc analysis whether the ANOVA analysis revealed significant, or marginally significant, interactions. The Spearman correlation was applied to explore the relation between self-reports and EEG data. The PANAS ratings were employed to defined the positive and the negative effects (PA and NA respectively). Scores of PA and NA for each participant and the choice of the songs among the two groups were correlated with the values of AW and Fmt.

Results

Figure 2:
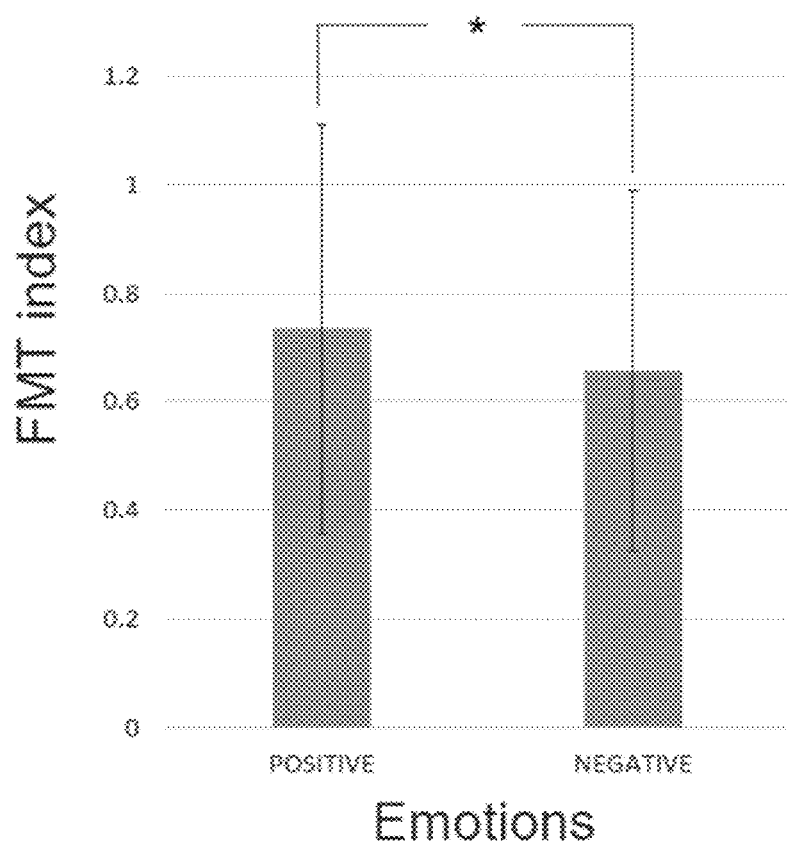
FIG. 2 is a representation of the Frontal Midline Theta Index (FMT): Fz electrode, theta band (IAF 6 to IAF 4).

The ANOVA conducted on the Fmt index exhibited a significant main effect of the emotional valence (F(1,12) =4.99; p=0.045). In line with our hypothesis, the index assumed higher values when the musical stimuli had positive valence rather than negative (FIG. 2). A marginally significant interaction was further observed between liking and emotional valence (F(1,12)=3.63; p=0.081), showing that the effect of the emotional valence on Fmt was more pronounced for listening to liked songs compared to the loved ones.

Figure 3:
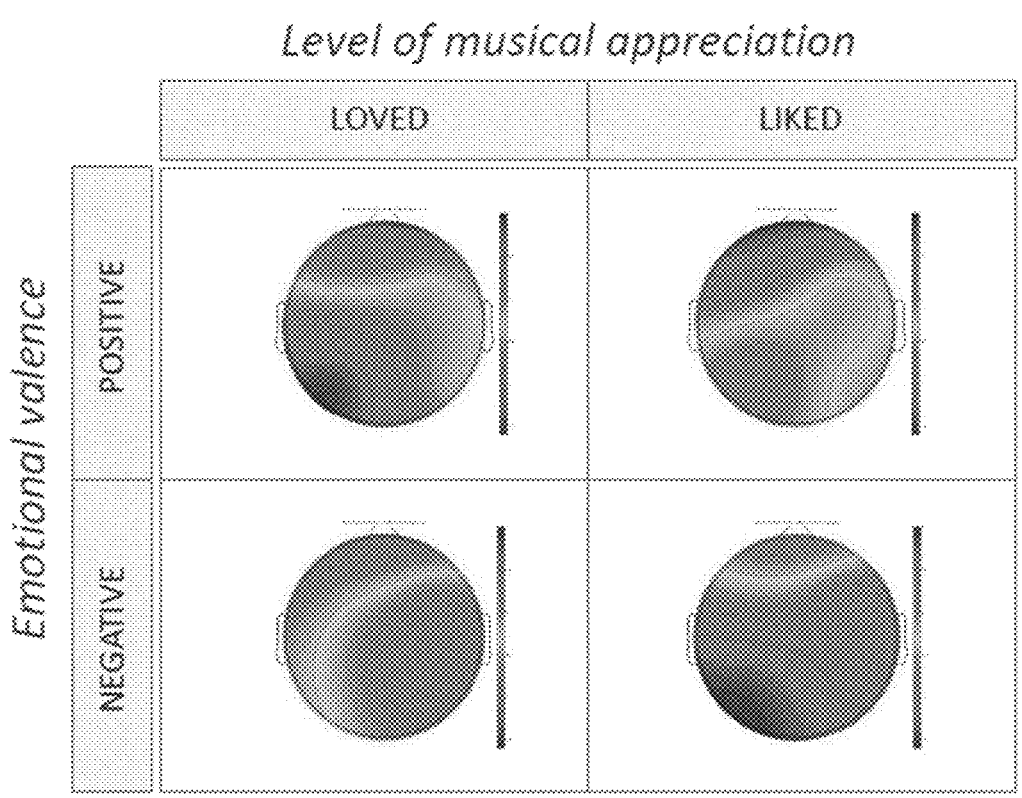
FIG. 3 is a topographical distribution of the mean Theta Power [dB] for the different conditions.
Figure 5:
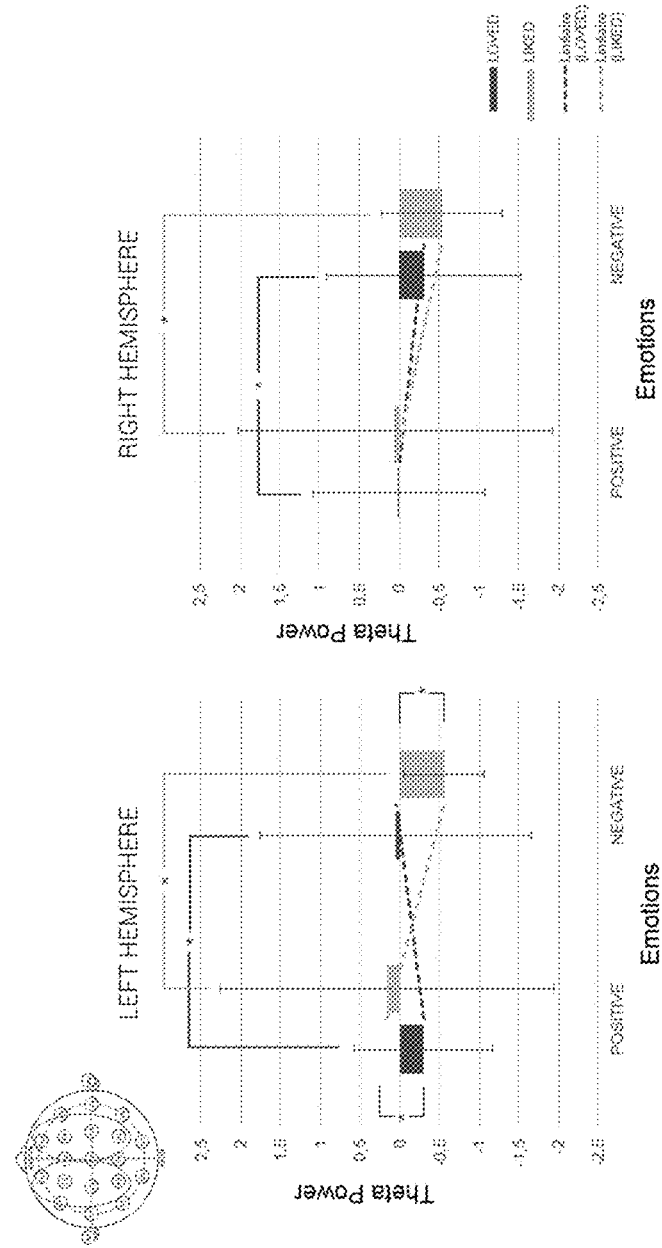
FIG. 5 is a representation of the mean Theta Power [dB] over all the electrodes.

Analyzing the modulation of the general theta power (IAF−6 Hz to IAF+4 Hz) over all the electrodes, we found a significant interaction (F(1,11)=5.41; p=0.04) across laterality, liking and emotional valence. While theta power for liked songs decreased from positive to negative emotions in both the hemispheres ($p_{left}$=0.001; $p_{right}$=0.005), the theta power for loved songs exhibited an opposite pattern in the two hemispheres (FIGS. 3 and 5). Specifically, comparing positive with negative emotions, we observed that it tended to increase in the left hemisphere ($p_{left}$=0.06) while it tended to decrease in the right ($p_{right}$=0.09).

Figure 1:
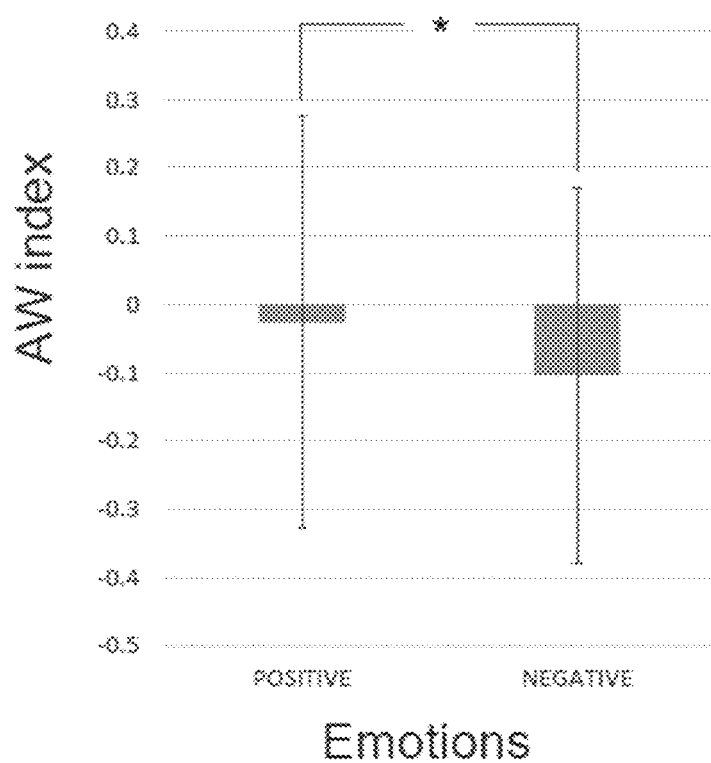
FIG. 1 is a representation of the Approach Whithdrawal Index (AW): Prefrontal electrodes, alpha band (IAF 0.2*IAF).

A two-ways ANOVA revealed a main effect of the emotional valence on AW index (F(1,11)=10.85; p=0.007). The index assumed in average higher values in listening to songs with positive valence, compared to the negative ones (FIG. 1). Analyzing the alpha asymmetry over the other couples of electrodes we did not find any significant results.

Figure 4:
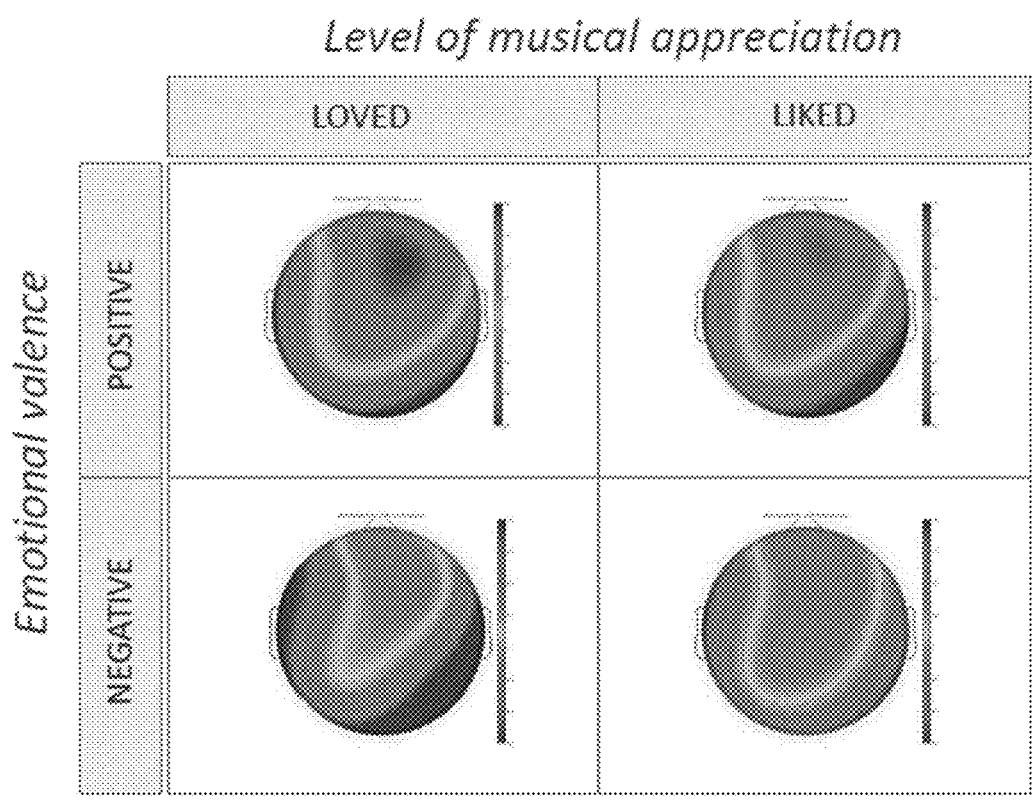
FIG. 4 is a topographical distribution of the mean Alpha Power [dB] for the different conditions.
Figure 6:
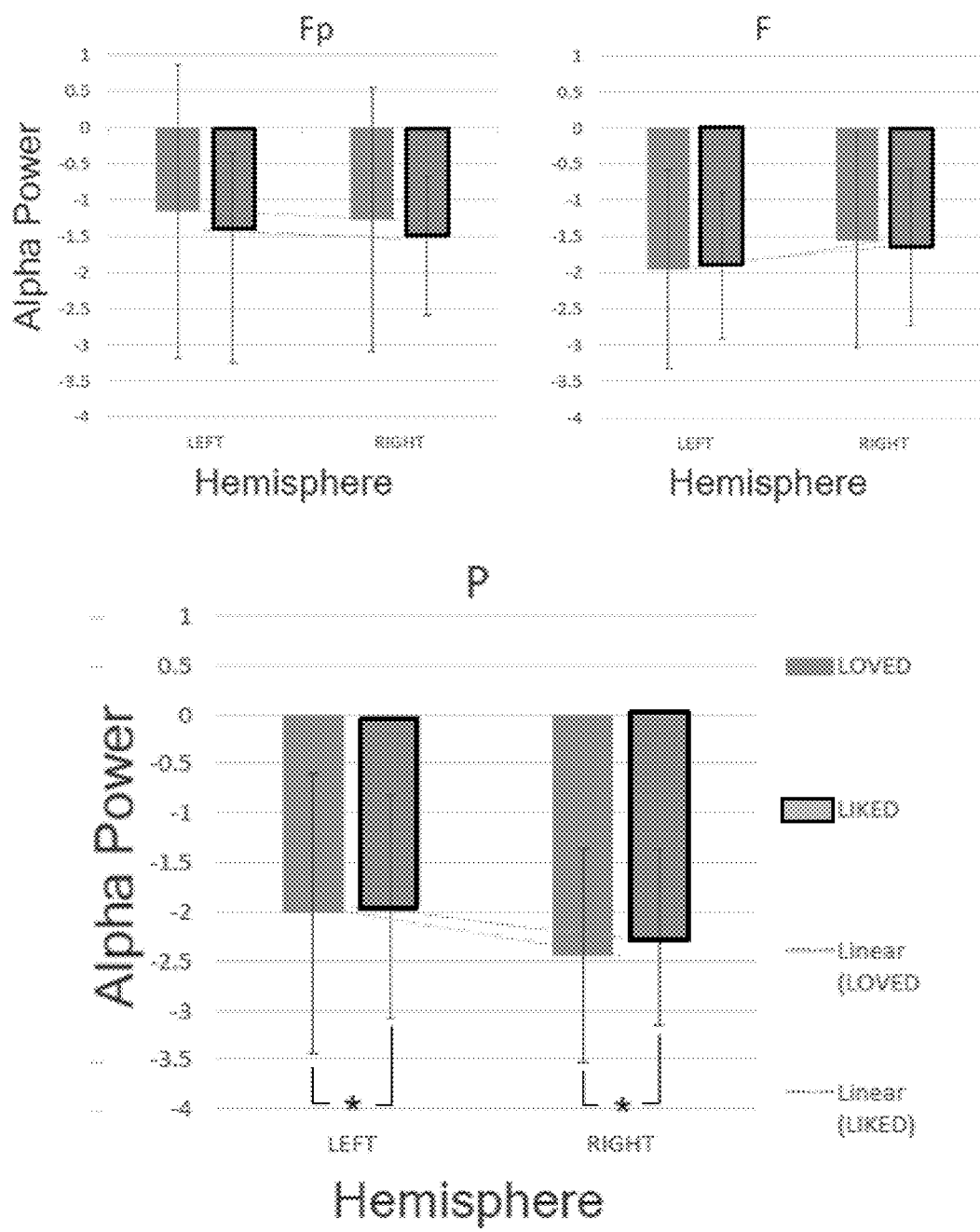
FIG. 6 is a representation of the mean Alpha Power [dB] over the electrodes in the left and in the right hemispheres.

The analysis of alpha power over all the electrodes showed significant interaction between scalp regions, laterality and liking (F(2,22)=4.59; p=0.022). By mean of post-hoc analysis we found that over parietal electrodes, in both left and right hemispheres (FIGS. 4 and 6), alpha power was higher for liked songs compared to the loved ones ($p_{left}$=0.038, $p_{right}$<0.001). Furthermore, for both liked and loved songs, alpha power over parietal electrodes was significantly higher in the left hemisphere compared to the right one ($p_{liked}$<0.001, $p_{loved}$<0.001).

No significant correlations were observed neither between the self-reports data and AW values, nor between self-report data and Fmt values. However, we found that ΔAW significantly correlated with the choice of the songs among the LOVED group (R=−0.537, p=0.04).

Discussion

The purpose of the present study was to investigate the brain signature underlying the emotions associated to the music and whether the emotional processes depend from the level with which the music is appreciated.

Figure 7:
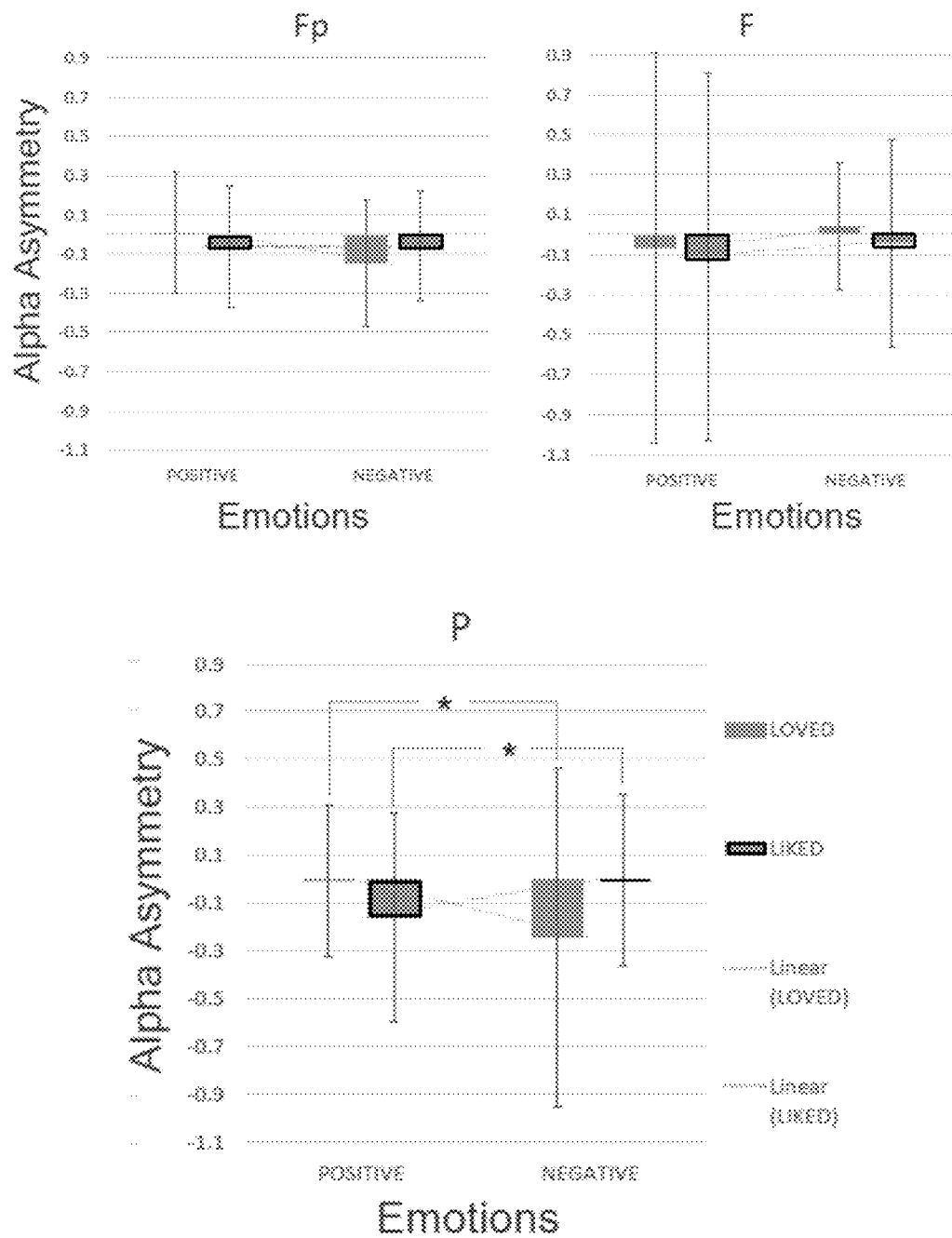
FIG. 7 is a representation of the alpha Asymmetry [dB] over couples of electrodes in prefrontal, frontal and parietal regions.

In line with our assumptions, both the AW and the Fmt indexes exhibited a good reliability in detecting the valence of the emotions evoked from the musical stimulations. The alpha asymmetry, as well as the frontal theta power, assumed discernible values according to the feelings, positive or negative, that participants associated to songs. In particular, we observed that positive emotions drove the prefrontal alpha asymmetry to the left, increasing the frontal midline theta power (FIG. 7). Opposite patterns were exhibited in listening to songs previously evaluated as negative. Through these results we confirmed that EEG analysis was efficient in determining brain mechanism that regulate the emotional response in musical listening. Otherwise, no effect was observed for discriminating the levels of liking. This lack of evidences could be explained by the fact that no disliked songs were employed in the stimulation. Loving and liking conditions were eliciting similar reactions in listeners, therefore their effect was not easy to distinguish, especially considering the small population of participants. Additionally, some participants declared that in the period between the phase of stimuli selection and the EEG experiment, their level of musical appreciation changed for some songs. Although we did not find any main effect of liking, some significant interactions showed that the level with which participants appreciated the songs modulated in some way both alpha and theta powers. In our hypotheses alpha power over prefrontal electrodes might have been informative for describing the intensity of the emotions felt. The difference of alpha power, observed for the two levels of musical appreciations, might hence indicate that loved songs were suitable to evoke more intense emotions than the liked ones. Furthermore, the same trend of alpha power was found also over parietal electrodes and it could imply that participants might have been more involved in listening to the excerpts they loved, necessitating a higher allocation of neuronal resources. The interactions found in theta band were not expected. While listening to liked songs generated a specific power trend in both hemispheres, the loved songs elicited opposite patterns of theta powers among left and right hemispheres in dependence of the emotions felt. These evidences are not easy to explain but they might implicate that participants employed different strategies in evaluating the emotional valence of the music, according to the levels with which they appreciated it. In particular, we assumed that participants could not avoid to rely on memories and personal experiences in evaluating songs they loved; although they were explicitly asked to base their judgments on musical features and lyrics. Therefore, the different reaction observed to musical stimulation might be sought in the hypothesis that some songs are loved right due to their association to the events of our life. The absence of significant correlation between electrophysiological values and self-ratings might be addressed to the particular context in which the experiment was conducted. In fact, all the participants knew the experimenters and this factor might have influenced their answers to the questionnaires. Furthermore, a tendency of significance was observed between alpha asymmetry and PANAS scores, probably, having had more data we would have found a significant correlation.

The invention claimed is:

1. A method for generating a personalized playlist of sounds for a subject using the analysis of said subject's electroencephalographic signal, said method comprising:
    receiving at least one segment of electroencephalographic signal acquired from at least one electrode while the subject is listening to at least one proposed sound;
    extracting at least one EEG index from the electroencephalographic signal segment so as to characterize brain patterns correlated to emotions evoked by said at least one proposed sound and a level of appreciation of said at least one proposed sound;
    evaluating a valence of sound listening for said at least one proposed on the basis of the EEG index;
    receiving a score of appreciation on said at least one proposed sound from the subject; and
    adding said at least one proposed sound in the personalized playlist of the subject whenever the valence matches a predefined valence and/or the score of appreciation is higher than a predefined threshold.

2. The method according to claim 1, wherein the EEG index is chosen among the following: Approach-Withdrawal index, the Frontal-Midline theta index, the prefrontal alpha power and/or the right parietal alpha power.

3. The method according to claim 1, wherein the at least one proposed sound is selected from a database of sounds and it is unknown to the subject.

4. The method according to claim 3, wherein the at least one proposed sound is selected from the database of sound using a sound selection algorithm, said sound selection algorithm being configured to identify in the sounds added in the personalized playlist, on the basis of the score of appreciation, at least one specific pattern and select from the database of sounds at least one sound with a similar specific pattern.

5. The method according to of claim 1, wherein each sound added in the personalized playlist is stored in a personal database with the score of appreciation and the EEG index.

6. A non-transitory computer-readable storage medium comprising instructions which when executed by a computer, cause the computer to carry out the method according to claim 1.

7. A system for generating a personalized playlist of sounds for a subject comprising:
at least one input adapted to receive:
at least one segment of electroencephalographic signal acquired from at least one electrode while the subject is listening to at least one proposed sound;
a score of appreciation on said at least one proposed sound from the subject;
at least one processor configured to:
extract at least one EEG index from the electroencephalographic signal segment so as to characterize brain patterns correlated to emotions evoked by said at least one proposed sound and a level of appreciation of said at least one proposed sound;
evaluate a valence of sound listening for said at least one proposed on the basis of the EEG index;
add said at least one proposed sound in the personalized playlist of the subject whenever said valence matches a predefined valence and/or the score of appreciation is higher than a predefined threshold; and
at least one output adapted to provide the personalized playlist.

8. The system of claim 7, further comprising at least one electrode for acquiring at least a segment of electroencephalographic signals from a subject and an audio-headset for producing the sounds.

9. The system of claim 7, wherein the EEG index is chosen among the following:
Approach-Withdrawal index, the Frontal-Midline theta index, the prefrontal alpha power and/or the right parietal alpha power.

10. The system of claim 7, wherein the at least one processor is further configured to select the at least one proposed sound from the database of sound using a sound selection algorithm.

11. The system of claim 10, wherein the sound selection algorithm is configured to identify in the sounds added in the personalized playlist, on the basis of the score of appreciation received for the added sounds, at least one specific pattern of each sound and select from the database of sounds at least one sound with a similar specific pattern.

12. A method for selecting from a personalized playlist of sounds of a subject a sub-group of sounds according to an emotional state of a subject:
receiving an information concerning the subject's emotional state defined by the subject;
selecting at least one sound from the personalized playlist and play it to the subject;
receiving at least one segment of electroencephalographic signal acquired from at least one electrode while the subject is listening to the selected sound; and
calculating the value of the Approach-Withdrawal index and whenever the Approach-Withdrawal index is greater that a predefined threshold, adding the selected sound to a sub-group of sounds associated to the type of emotional state defined by the subject.

13. A non-transitory computer-readable storage medium comprising instructions which when executed by a computer, cause the computer to carry out the method according to claim 12.

14. A system for selecting from a personalized playlist of sounds of a subject a sub-group of sounds, said system comprising:
at least one input adapted to receive:
an information concerning the subject's emotional state defined by the subject;
at least one processor configured to:
selection of at least one sound from the personalized playlist and play it to the subject;
calculating the value of the Approach-Withdrawal index for at least one segment of electroencephalographic signal acquired from at least one electrode while the subject was listening to the at least one selected sound; and
add the at least one selected sound to a sub-group of sounds associated to the type of emotional state defined by the subject whenever said Approach-Withdrawal index is greater that a predefined threshold.

15. The system of claim 14, further comprising at least one electrode for acquiring at least a segment of electroencephalographic signals from a subject and an audio-headset for producing the sound.

* * * * *